US 8,713,862 B2

(12) United States Patent
Sondermann (10) Patent No.: US 8,713,862 B2
(45) Date of Patent: May 6, 2014

(54) DEVICE FOR SECURING THE EDGE OF A FLOOR COVERING TO A PROFILE CONSTRUCTION (75) Inventor: Frank Sondermann, Lüdenscheid (DE)

(73) Assignee: Kuberit Profile Systems GmbH & Co. KG, Ludenscheid (DE)

(*) Notice: Subject to any disclaimer, the term of this patent is extended or adjusted under 35 U.S.C. 154(b) by 7 days.

(21) Appl. No.: 13/375,727

(22) PCT Filed: May 10, 2010

(86) PCT No.: PCT/EP2010/056383
§ 371 (c)(1),
(2), (4) Date: Apr. 3, 2012

(87) PCT Pub. No.: WO2011/003650
PCT Pub. Date: Jan. 13, 2011

(65) Prior Publication Data
US 2012/0186171 A1   Jul. 26, 2012

(30) Foreign Application Priority Data

Jul. 9, 2009  (DE) .................. 10 2009 032 673
Jul. 9, 2009  (DE) .................. 20 2009 017 769 U (51) Int. Cl.
E04F 11/16  (2006.01)
E04F 15/00  (2006.01)

(52) U.S. Cl.
USPC ........................................................ 52/179

(58) Field of Classification Search
USPC ............ 52/179, 177, 181, 459, 466, 469, 470
See application file for complete search history.

(56) References Cited

U.S. PATENT DOCUMENTS 4,455,797 A * 6/1984 Naka ............................... 52/179
4,858,404 A * 8/1989 Schluter ......................... 52/179

(Continued)

FOREIGN PATENT DOCUMENTS

AT      10 366 U1     2/2009
DE   102 46 968 A1    5/2004

(Continued)

OTHER PUBLICATIONS

International Search Report (in German with English translation) and Written Opinion (in German) for PCT/EP2010/056383, mailed Oct. 15, 2010; ISA/EP.

Primary Examiner — Brian Glessner
Assistant Examiner — Paola Agudelo
(74) Attorney, Agent, or Firm — Harness, Dickely & Pierce, P.L.C.

(57) ABSTRACT

A device for removably securing the edge, provided with a profiling, of a floor covering to a profile construction delimiting the floor covering, the profile construction being in particular a step nosing profile with an angular step profile and a base profile which can be secured on a step and the angular step profile having a step leg with a covering wing and a stop leg, wherein an interchangeable insert which is configured as a profile rail and is arranged such that it can be removed and can be adapted in its position to the profile construction and on which is configured, at least on one of its two mutually opposite longitudinal edges, a retainer which cooperates with the profiling of the edge of the floor covering and is configured to be at least partly complementary to the profiling.

17 Claims, 6 Drawing Sheets (56) References Cited

U.S. PATENT DOCUMENTS

| | | | |
|---|---|---|---|
| 6,038,733 A * | 3/2000 | Carder et al. | 16/16 |
| 6,101,770 A * | 8/2000 | Dalton | 52/179 |
| 6,127,015 A * | 10/2000 | Kessler | 428/45 |
| 6,141,920 A * | 11/2000 | Kemper | 52/179 |
| 7,389,613 B2 * | 6/2008 | Sondermann | 52/179 |
| 7,966,781 B2 * | 6/2011 | Muehlebach | 52/177 |
| 2006/0207198 A1 * | 9/2006 | Sondermann | 52/220.1 |
| 2009/0071089 A1 * | 3/2009 | Neuhofer, Jr. | 52/469 |
| 2011/0283636 A1 * | 11/2011 | Vanhastel | 52/179 |

FOREIGN PATENT DOCUMENTS

| | | |
|---|---|---|
| JP | 52 116612 A | 9/1977 |
| JP | 55 121832 U | 8/1980 |
| JP | 56 038687 U | 4/1981 |
| JP | 56038687 U * | 4/1981 |
| JP | 2005 207063 A | 8/2005 |
| WO | WO-2005/065381 A2 | 7/2005 |
| WO | WO-2007-048157 A1 | 5/2007 |

* cited by examiner

DEVICE FOR SECURING THE EDGE OF A FLOOR COVERING TO A PROFILE CONSTRUCTION

CROSS-REFERENCE TO RELATED APPLICATIONS

This application is a 371 U.S. National Stage of International Application No. PCT/EP2010/056383, filed May 10, 2010, and claims priority to German patent application Nos. 10 2009 032 673.1 filed Jul. 9, 2009 and 20 2009 017 769.6, filed Jul. 9, 2009, the disclosures of which are herein incorporated by reference in their entirety.

The invention relates to a device for removably securing the edge, provided with a profiling, of a floor covering to a profile construction which delimits the floor covering, said profile construction being in particular a step nosing profile with an angular step profile and a base profile which can be secured on a step and the angular step profile comprising a step leg with a covering wing and a stop leg.

In the prior art, profile constructions are known which are provided on the edges of a floor covering to protect said floor covering from becoming detached from the floor at the edge. The edge of the floor covering is exposed to a particular stress because, if unprotected, it can easily get pushed back. Therefore, profile constructions are used in critical areas and are applied, for example, on stair nosings or on transitions to other floor coverings.

EP 773 335 discloses a step nosing profile which consists of two elements, namely an angular step profile and a base profile. Formed on the angular step profile is a step leg which has on its free end a covering wing for a step covering. The angular step profile is positioned on the base profile which can be secured on the edge region of the step and has a stop leg which projects downwards at a right angle on the step leg and also has an additional web in a spacing thereto. After the angular step profile has been attached, the step covering is overlapped by a predetermined extent by the covering wing, thereby reliably preventing the edge of the step covering from lifting up or being pushed back.

This device operates in a satisfactory manner, particularly when the step covering can be pushed back by a specific extent so that the outer edge of the covering wing can slightly penetrate inside the covering, thus preventing the formation of a noticeable joint between the surface of the covering and the angular step profile. In the case of a parquet floor or a laminated floor covering, penetration into the floor covering is not possible unless the peripheral region is provided with a suitable milled-out portion for the covering wing. However, at the construction site, this is only possible under difficult conditions or is not possible at all.

Therefore, the object of the invention is to provide a device for securing a floor covering to a profile construction, by means of which an edge, provided with a profiling, of the floor covering can be held securely and permanently while avoiding an attachment joint.

The object is achieved according to the invention by an interchangeable insert which is configured as a profile rail, is arranged such that it can be removed and can be adapted in its position to the profile construction and on which is configured, at least on one of its two mutually opposite longitudinal edges, a retainer which cooperates with the profiling of the edge of the floor covering and is at least partly formed in a complementary manner to the profiling. The fact that the edge of the floor covering, provided with a profiling, can cooperate with the complementary retainer means that a secure retention of the free edge of the floor covering is provided and the free edge is prevented from being able to lift up from the floor.

In an advantageous configuration, the interchangeable insert is completely or partly arranged between the step leg and the base profile, said interchangeable insert preferably having different retainers to be used on different profilings of tongue and groove joints on both of its mutually opposite longitudinal edges. This particular arrangement provides a secure and unalterable positioning of the interchangeable insert on the step nosing profile.

In a particularly advantageous configuration, the interchangeable insert is held on the profile construction by a lock. As a result, it is optionally possible first to insert the interchangeable insert into the profile construction and then to attach the edge of the floor covering, or else initially to produce a join with the edge profile and subsequently to produce the join with the profile construction.

In this respect, it is advantageous if the interchangeable insert has, as part of the lock in the region of the complementary retainer, an anchorage with the base profile and/or the step leg. This ensures that the floor covering cannot change with respect to the device.

The interchangeable insert is advantageously provided with at least one supporting rib which has on its free supporting edge a locking engagement which cooperates with a corresponding locking engagement on the base profile. This supporting rib is able to support the angular step profile in the region of the step leg or covering wing so that the step leg cannot be trodden down. This risk would exist because in the invention, the step leg no longer overlaps the floor covering but merely meets the edge thereof and no longer rests thereon. The lock produces a permanent positional fixing so that the interchangeable insert cannot slip.

Advantageously configured on the supporting rib is a web which serves to absorb horizontal forces and which is adjoined by the complementary retainer. As a result, the forces acting on the floor covering can be introduced into the device via the complementary retainer and the web as well as the supporting rib.

A favorable configuration can provide the production of the interchangeable insert as a strand cast profile of aluminium or plastics material. This results in a cost-effective production.

The profiling of the edge of the floor covering and thus the corresponding partially complementary retainer can be partly or completely configured in a type of tongue and groove joint which has at least one projection which is prominent relative to the tongue and groove plane and has a recess.

In this respect, it is advantageous if the complementary retainer has at least one retaining rib or one retaining projection which upwardly secures the tongue and groove joint and/or at least to some extent engages behind the projection or engages in the recess. A configuration of this type can advantageously be provided such that predetermined breaking points for height reduction are formed on the at least one retaining rib or the retaining projection. In this respect, in the delivery condition, the retaining rib can have a height which substantially corresponds to the thickness or to an approximate thickness of a conventional profile. Depending on the particular configuration of the tongue and groove form, this retaining rib can then be reduced in height until it can engage, fitting, into the recess or can engage behind the projection, thus forming a secure anchorage. Even if the tongue and groove joint comprises a tongue in the form of a normal projecting rib, the retaining rib formed on the interchangeable insert is able to secure the peripheral region of the floor covering insofar as it can rest against the tongue and, while so doing, can exert a downwardly directed pressure.

A particularly simple configuration is one in which the interchangeable insert is substantially U-shaped and one leg of the U is configured as a retaining rib and the other leg of the U is configured as a supporting rib. In this embodiment, both legs are joined together by the web. In this respect, it can be favorable for both legs to have predetermined breaking points so that they can be adapted to the height of the floor covering and consequently can be used for different profile constructions.

Finally, in a further alternative embodiment, the interchangeable insert can be provided with a hole to secure it by an attachment means to a straight edge of a floor covering, i.e. if the floor covering does not have a projecting profiling on the edge, but a smooth end face.

In a further advantageous embodiment, the interchangeable insert can be held on the base profile by a rail guide system. Thus, the interchangeable insert can be pre-assembled with the base profile, handling being simplified because only one component consisting of interchangeable insert and base profile has to be managed.

It is favorable for the rail guide system to have a rail arrangement which is spherical in cross section. However, it can also be advantageous to provide a dovetail joint for the rail guide system. Both types of connection can provide a simple, light, fast and stable join between the interchangeable insert and the base profile. The advantage of the spherical shape over the dovetail is seen in the impact-resistant shape, since no edges or corners can be damaged during installation. On the other hand, the dovetail is simple to produce, which means a corresponding reduction in costs.

Furthermore, in the case of a spherical shape, the interchangeable insert can be pushed under pressure into a complementary groove in the base profile, so that precise positioning is unnecessary because the mutually associated individual elements inevitably find a snug fit.

In the following, the invention will be described in more detail with reference to embodiments illustrated in the drawings, in which.

Figure 1:
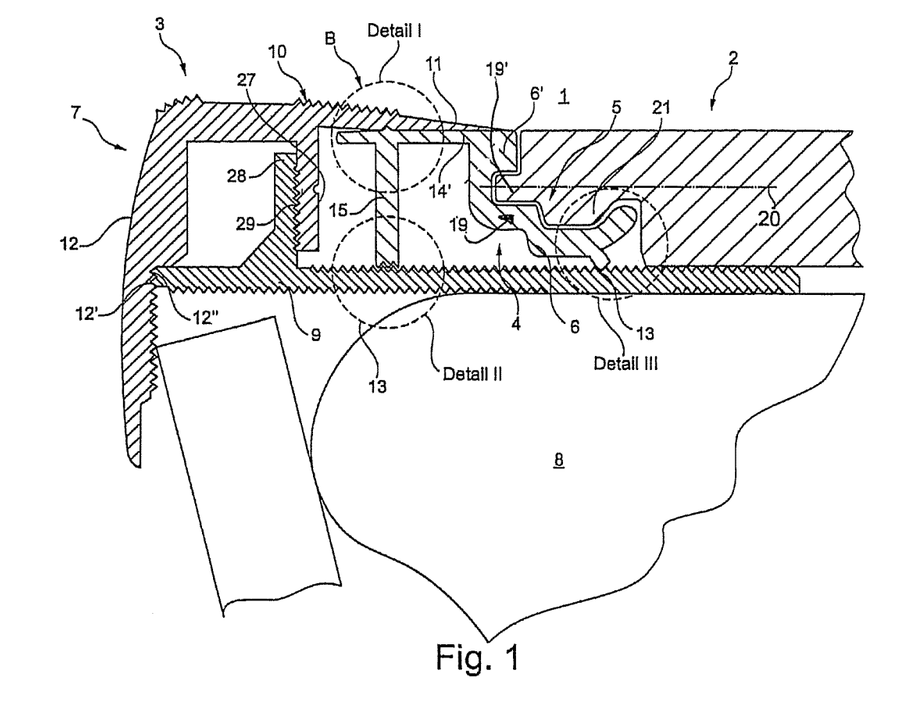
FIG. 1 shows a device according to the invention which is configured as a step nosing profile and has a clicked-in floor covering.

FIG. 1 shows a device for removably securing the edge 1 of a floor covering 2 to a profile construction 3. The floor covering consists of elements which are joined together and are provided on their edge with a profiling in the sense of a tongue and groove system, thereby ensuring a fixed join of the individual elements. In the illustrated embodiment, the profile construction 3 is a step nosing profile, comprising an angular step profile 7 and a base profile 9 which can be secured on the tread of a step 8. The angular step profile 7 has a substantially horizontal step leg 10 with a covering wing 11 and a vertically extending stop leg 12.

The stop leg 12 is provided with a profiling 12' which cooperates with a corresponding profiling 12" on the leading edge of the base profile 9. The angular step profile 7 is provided on its lower side with a stop rib 27 which comes to rest against a counter rib 28 which projects upwards on the base profile 9. A lock 29 is formed between the two ribs. Thus, the angular step profile 7 can be locked at any height on the base profile 9 so that as a result, an adaption can be made to the thickness of the floor covering 2.

According to the invention, the profile construction 3 configured as a step nosing profile has the interchangeable insert 4 which is configured as a profile rail and is arranged such that it can be removed and adapted in its position to the profile construction 3. Furthermore, configured on the interchangeable insert 4 is a retainer 6 which at least partly complements the profiling 5 of the edge 1 of the floor covering 2 and cooperates with the profiling 5 of the edge 1 of the floor covering 2 on one of its two mutually opposite longitudinal edges.

As shown by the further embodiments described in more detail below, the retainer 6 can also be configured such that it is adapted to be only partly complementary to the profiling 5 or to the contour of the tongue and groove joint.

In the illustrated embodiment, the profiling is part of a particular tongue and groove joint 19, the tongue 19' of which projects forwards on the edge of the floor covering 2. The profiling 5 also has a recess, as a result of which a shoulder is produced on the edge of the floor covering. Formed on this shoulder is a projection 21 which projects over the tongue and groove plane 20. A recess 22 is formed downstream of the projection 21. In the embodiment illustrated in FIG. 1, the complementary retainer 6 of the interchangeable insert 4 is configured such that its contour corresponds to the counterpart of the tongue and groove joint 19. As can be seen in detail III in FIG. 2c, the retainer 6 therefore has on its free end facing the floor covering a retaining projection 23 which encompasses the projection 21 and engages in the recess 22 in the tongue and groove joint 19.

In detail, the interchangeable insert 4 consists of a profile which can be used as a rail or in individual pieces. As can be seen in particular from FIG. 1, the retainer formed on the profile continues upwards on its sides facing the step nosing profile and, in so doing, engages around the tongue 19'. A web 14 then extends substantially in the horizontal direction and a supporting rib 15 is formed thereon which is positioned substantially at a right angle on the web 14 in a spacing from the retainer 6.

The supporting rib 15 which has a locking engagement 17' on its free supporting edge 16 cooperates with a corresponding locking engagement 17" on the base profile 9.

In the illustrated embodiment according to FIG. 1, the profile of the interchangeable insert 4 is partly arranged between the step leg 10 and the base profile 9 and projects into the floor covering 2 with its region configured as a complementary retainer 6 at one of the two mutually opposite longitudinal edges. Thus, there is engagement behind the projection 21 set back into the floor covering 2 relative to the projecting tongue 19' as a result of engagement into the recess 22.

The interchangeable insert 4 is joined in a detachable manner to the profile construction 3 and held thereon by lock 13. In the illustrated embodiment, the lock 13 engages at three points on the profile construction. The points are identified in FIG. 1 by detail I, detail II and detail III and are illustrated in the corresponding FIGS. 2a to 2c.

Figure 2A:
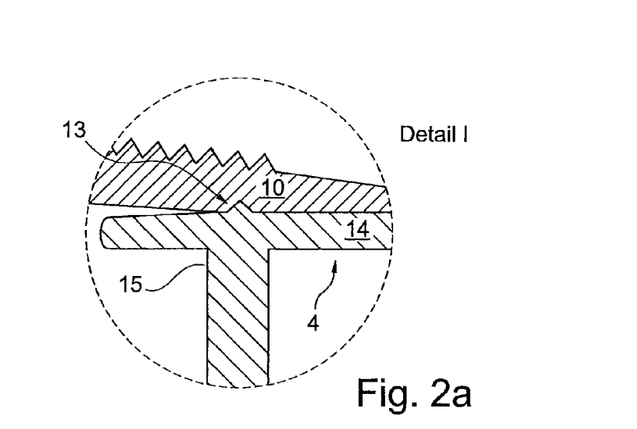
FIG. 2a-2c show details 1 to 3 from FIG. 1.

In FIG. 2a, detail I is reproduced on an enlarged scale. In this embodiment, the web 14 of the interchangeable insert 4 comes to rest substantially in a planar manner under the step leg 10 and the covering wing 11. In the region of the step leg 10, the web 14 has a lock 13 consisting of a locking rib and a correspondingly formed locking groove. In the illustrated embodiment, the locking rib is formed on the web 14 and the locking groove is formed accordingly in the lower side of the step leg. This lock is preferably located substantially above the supporting rib 15 which projects vertically downwards from the web 14.

Figure 2B:
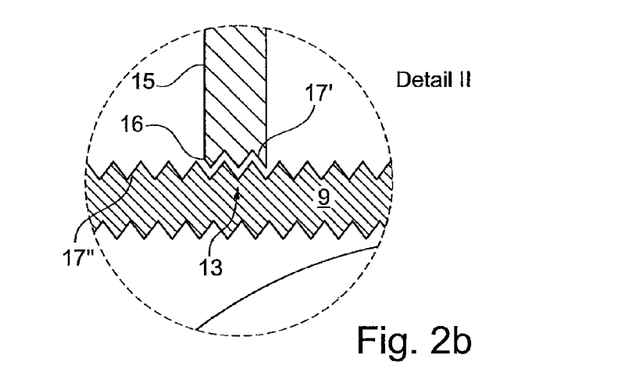

FIG. 2b shows detail II in which the lower end portion of the supporting rib 15 is illustrated with the lock 13 located there. A supporting edge 16 of the supporting rib 15 is provided with a locking engagement 17' which cooperates with a corresponding locking engagement 17" on the surface of the base profile 9. The positional measurements are selected such that the lock 13 engages on the web 14 when the locking engagements 17', 17" are also interlocked.

Figure 2C:
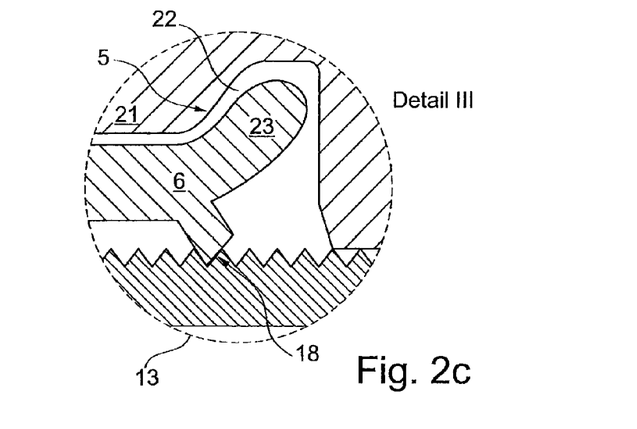

In FIG. 2c, the third lock 13 is shown in detail III. In this case, the interchangeable insert 4 has, as part of the lock in the region of the complementary retainer 6, an anchorage 18 where locking grooves on the base profile provide an engagement for an anchoring projection. In addition or instead, the interchangeable insert 4 can have an anchorage 18 with the step leg 10 (not shown).

As a result of the three-point anchorage, the interchangeable insert 4 is held independently and securely in position irrespective of its engagement with the profile of the floor covering when the angular step profile is locked onto the base profile. In this respect, it is possible to select a locking position in which the profile of the interchangeable insert 4 is clamped under pressure between the step leg 10 and the base profile 9. Due to the lock of the interchangeable insert 4, the web 14 can absorb horizontal forces which are introduced into the step nosing profile arrangement 3 from the floor covering via the complementary retainer 6 and the supporting rib 15.

In particular embodiments, the rib of the anchorage 18 can have a longer length than is shown. The supporting rib 15, like the downwardly projecting rib which is used as the anchorage 18, can then also be provided with predetermined breaking points, thereby allowing a reduction in height or an adaptation to the thickness of the floor covering.

Figure 3:
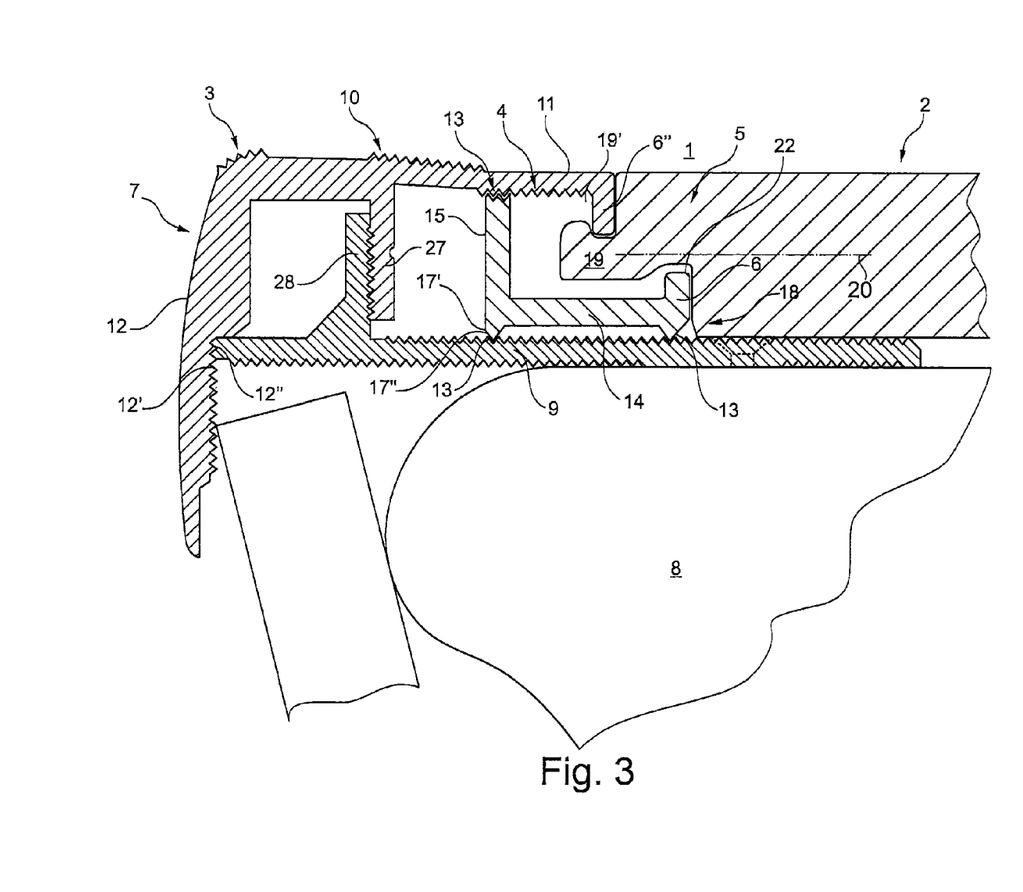
FIG. 3 shows the next embodiment of the invention used for a step nosing profile, with a different profiling of the floor covering.

FIG. 3 shows the next embodiment of the invention. In this embodiment the elements, which perform the same function as in the device of FIG. 1, are provided with the same reference numerals.

In this embodiment, the interchangeable insert 4 is formed by a substantially L-shaped profile, the web 14 not coming to rest under the step leg, but being substantially arranged directly above the base profile 9. The supporting rib 15 is supported under the step leg 10 and on the base profile 9, again with a lock 13 or with a locking engagement 17' and 17". The web 14 extends in the direction of the tongue and groove joint 19 of the edge of the floor covering and it has on its free end a web, standing substantially vertically upwards, as a complementary retainer 6. This web engages behind a recess 22 provided in the tongue and groove joint 19. Formed under this web of the retainer 6 is the anchorage 18 of the lock 13 so that a three-point retention is ensured in this embodiment as well. For support against the step leg 10, an additional retaining rib 6" functioning as a web extension can be positioned on the tongue of the tongue and groove joint 19.

Figure 4:
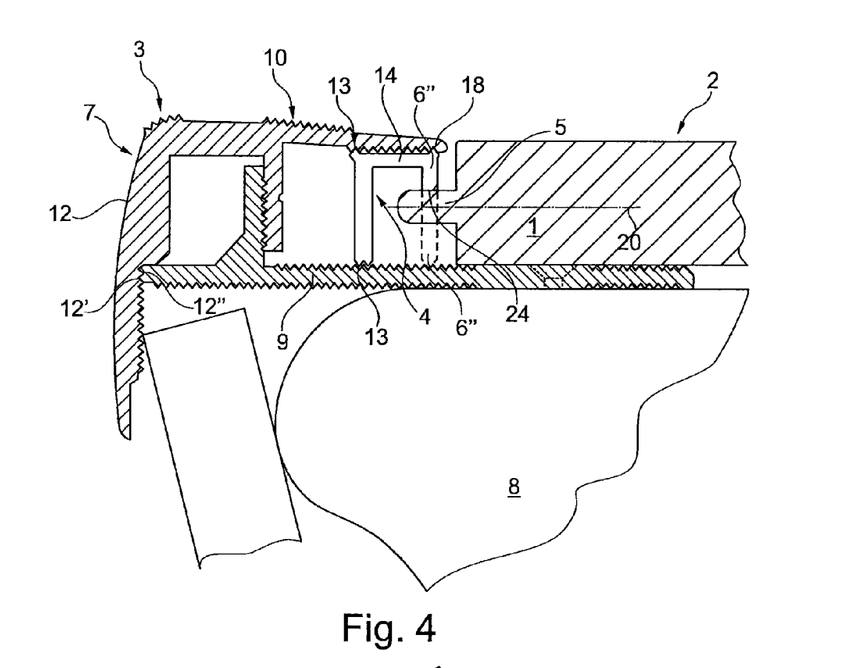
FIG. 4 shows the next embodiment with the next profiling of the edge of the floor covering.

FIG. 4 shows the next embodiment of a removable interchangeable insert 4. Features with the same reference numerals correspond to the features of FIG. 1 which have an identical function.

This variant also uses a substantially L-shaped profile of the interchangeable insert 4, although the base leg, forming the web 14, of the L-shaped profile comes to rest under the step leg 10 or covering wing 11 and is held on the step leg 10 by means of the lock or anchorage 13. The downwardly projecting supporting rib 15 is supported with the lower lock 13 on the base profile 9. In the present case, the complementary retainer 6 is configured as a downwardly projecting retaining rib 6" which has been reduced to a suitable measurement by breaking off the excess length, shown in dashed lines in FIG. 4, at a predetermined breaking point 24. In so doing, the web comes to rest against the profiling 5 of the tongue and groove arrangement and prevents the covering from lifting up.

Figure 5:
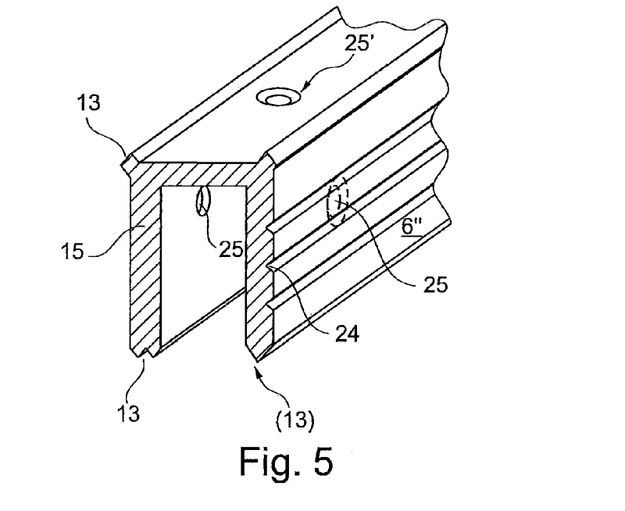
FIG. 5 is a perspective view of a substantially U-shaped interchangeable insert with a hole.
Figure 6:
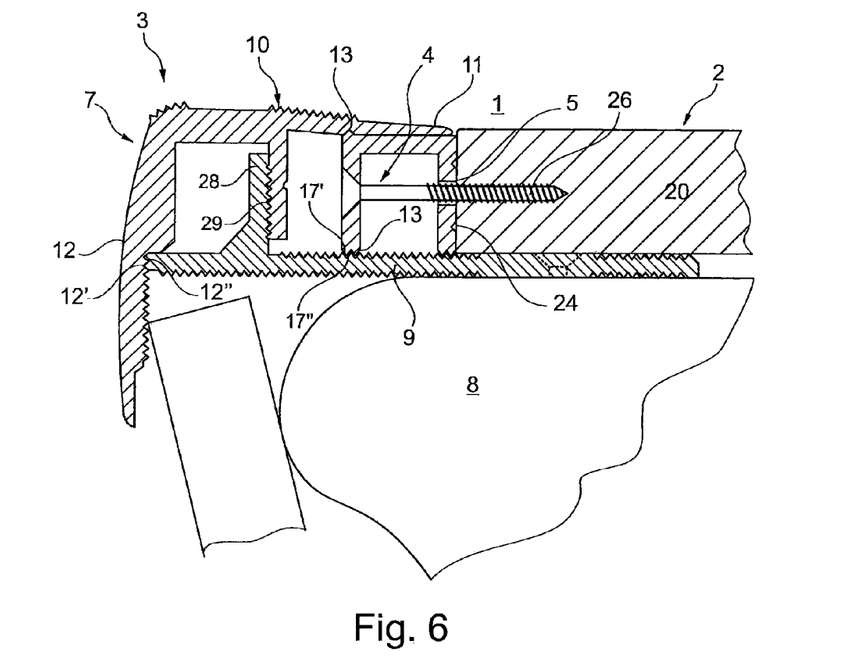
FIG. 6 shows the interchangeable insert from FIG. 5 in an installed state when used with a floor covering, the peripheral edge of which has a straight end face.

FIGS. 5 and 6 show a further embodiment of the invention. Features with the same reference numerals correspond to those in FIG. 1.

The profile of the interchangeable insert 4, shown in the embodiment according to FIG. 5, is substantially U-shaped or is configured as a U-profile in the form described here, with one leg of the U being configured as a retaining rib and the other leg of the U being configured as supporting rib 15. In this case, the downwardly projecting retaining rib 6" of the retainer 6 is of the same length as the supporting rib 15. The interchangeable insert is anchored to the step nosing profile again by the lock 13 which is configured on the edges of the U-shaped profile which cooperate in each case with corresponding locking ribs under the step leg 10 or the covering wing 11 and on the base profile 9. However, in this profile, a hole 25 is also formed which penetrates both legs of the U-shaped profile and is used to receive a screw by which the interchangeable insert can be secured to the end face of the straight edge of the floor covering.

As shown in FIG. 6, this embodiment is used particularly in the case of edges 1, the side face of which is not provided with a profiling. Such an interchangeable insert 4 can also be easily adapted to different heights of the floor covering 2 because its downwardly projecting U-shaped legs which are joined together by the web 14, can be brought, as required, to a suitable height at the predetermined breaking points 24.

Thus, this embodiment of the retainer is suitable for holding a floor covering with a smooth peripheral surface, without the covering wing 11 having to be applied on the floor covering, forming an abutment edge, and is also suitable, according to FIG. 4, for use in profiled tongue and groove-joined edges, in which case the retaining rib 6", facing the floor covering, is shortened to the appropriate measurement at the predetermined breaking points 24 to allow a corresponding tongue to rest on or against the shortened retaining rib 6".

It is understood that such a screw connection can also be used for a join according to FIG. 4, in which case the projecting tongue can be removed in the region of the screw.

Figure 7:
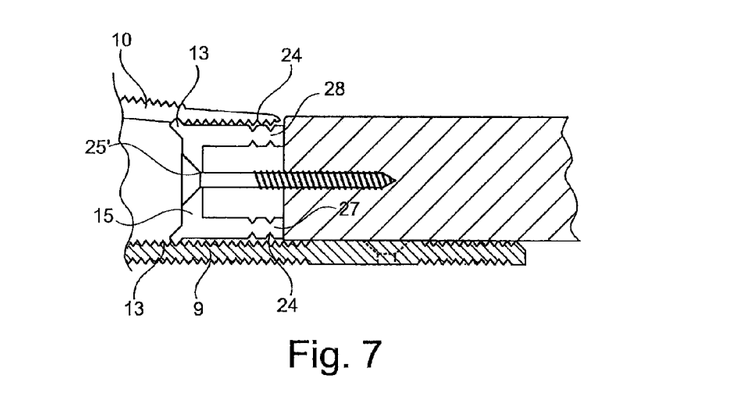
FIG. 7 shows the next embodiment with a horizontal, substantially U-shaped interchangeable insert.

FIG. 5 shows a further hole 25' which can be used if the U-shaped profile is used in a horizontal position and not in a vertical position, cf. FIG. 7. The lock 13 is configured such that, even in a horizontal position, it can engage in corresponding locking grooves under the step leg 10 and on the base profile 9. In this embodiment, the horizontal legs of the U-shaped profile can engage over the tongue and groove configuration and can abut the edge of the floor covering with both legs or with only one leg.

The join shown in FIG. 7 uses the embodiment illustrated in FIG. 5 with the hole 25' which is provided in the base of the U-shaped interchangeable insert substantially in the plane of symmetry. The legs 27 and 28 engage around a tongue of the tongue and groove joint and come to rest against the actual side face of the edge of the floor covering, and it is also possible to take account of the width of the tongue by shortening the legs.

Figure 8:
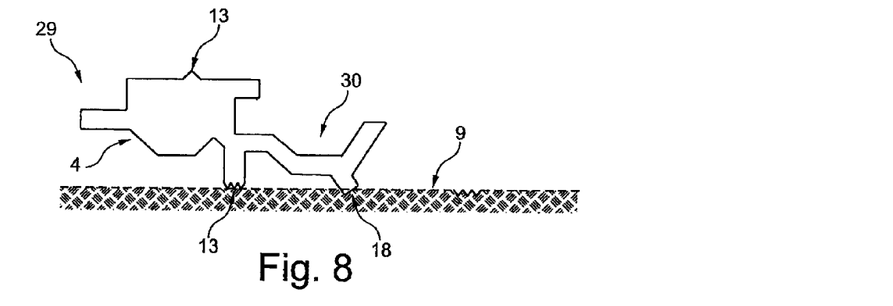
FIG. 8 shows an embodiment of an interchangeable insert with bilateral profiling for the groove side and for the tongue side.

FIG. 8 shows a further embodiment of an interchangeable insert 4. In this embodiment of an interchangeable insert, a profiling is formed for the groove side and for the tongue side in each case on a longitudinal side of a profile forming the interchangeable insert. Thus, it is possible to use the interchangeable insert irrespective of the nature of the profiling, without the craftsperson having to take care whether the groove side or the tongue side rests against the step nosing profile.

Figure 9:
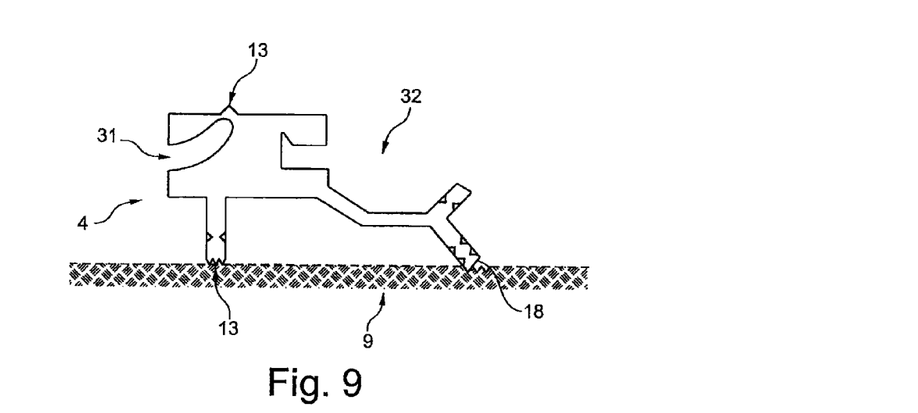
FIG. 9 shows an embodiment of an interchangeable insert with bilateral profiling to be used for different types of profiling.

FIG. 9 shows an embodiment of an interchangeable insert 4 with a bilateral profiling to be used for different types of profiling 31 and 32 which may be present in different types of floor coverings.

Figure 10:
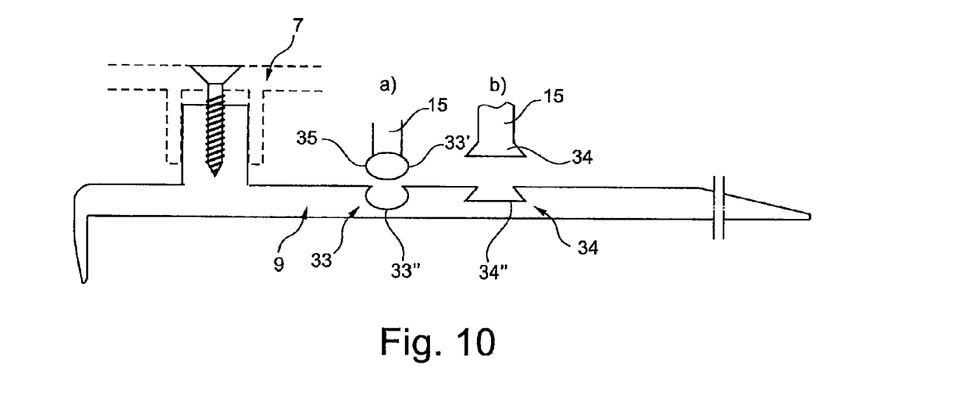
FIG. 10 shows different seats for attaching an interchangeable insert to a base profile.

Finally, FIG. 10 shows, by way of example, different rail guide systems 33, 34 for attaching an interchangeable insert 4 to a base profile. A rail guide system of this type replaces a lock or an anchorage.

The seat according to example a) has on the supporting rib 15 a substantially partly-cylindrical locking projection 33' which is pushed under pressure into the complementary groove 33" in the base profile 9. If the neck 35 is configured to be correspondingly narrow, it is also possible to introduce the interchangeable insert into the base profile from the side.

The embodiment according to example b) provides a dovetail joint 34, in which a dovetail guide 34" is formed in the base profile 9 and a dovetail 34' is formed on the supporting rib 15. In both embodiments, the interchangeable insert is arranged securely and always in the correct position.

It is understood that the dimensions, illustrated in the figures, of the embodiments do not necessarily have to correspond to the actual dimensions. Thus, for example, care must be taken in the case of the embodiments of FIGS. 8 and 9 that the dimensions of the interchangeable insert adequately consider the space under the step leg.

Furthermore, the profile construction illustrated in FIGS. 1 to 4 is not restricted to a locking join, but also includes constructions which use a screw connection between the angular step 7 and the base profile 9, as shown in FIG. 10.

LIST OF REFERENCE NUMERALS 1 edge
2 floor covering
3 profile construction
4 interchangeable insert
5 profiling
6 complementary retainer
7 angular step profile
8 step
9 base profile
10 step leg
11 covering wing
12 stop leg
13 lock
14 web
15 supporting rib
16 supporting edge
17 locking engagement (17', 17")
18 anchorage
19 tongue and groove joint
19' tongue
20 tongue and groove plane
21 projection
22 recess
23 retaining rib
24 predetermined breaking points
25 hole
26 attachment means
27 stop rib
28 counter rib
29 lock

The invention claimed is:

1. A device for removably securing an edge of a floor covering provided with an original profiling to a profile construction delimiting the floor covering,
the profile construction being a step nosing profile with an angular step profile and a base profile,
wherein the base profile can be secured on a step, and
the angular step profile having a step leg with a covering wing and a stop leg extending from a leading edge of the base profile,
wherein the device further comprises an interchangeable insert which is configured as a profile rail and is arranged such that it can be removed and can be adapted in its position to the profile construction, and
whereby said insert is configured with a first retainer on at least one of two mutually opposite longitudinal edges of the insert, whereby said first retainer cooperates with the original profiling of the edge of the floor covering to removably secure the insert to the floor covering, and
whereby the first retainer is configured to be at least partly complementary to the original profiling; and
wherein the interchangeable insert comprises at least one vertically extending supporting rib which has on its free supporting edge a locking engagement which cooperates with a corresponding locking engagement on the base profile.

2. The device according to claim 1, wherein the interchangeable insert is completely or partly arranged between the step leg and the base profile and has a second retainer to be used on the longitudinal edge opposite to the first retainer.

3. The device according to claim 2, wherein the interchangeable insert is held on the base profile by a guide rail system.

4. The device according to claim 1, wherein the interchangeable insert is held on the profile construction by means of a lock.

5. The device according to claim 4, wherein the interchangeable insert has, in a region of the first retainer, an anchorage with at least one of the base profile and the step leg whereby the anchorage is part of the lock.

6. The device according to claim 4, wherein the interchangeable insert is held on the base profile by a rail guide system.

7. The device according to claim 1, wherein the at least one vertically extending supporting rib has a web which is used to absorb horizontal forces and which is adjoined by the first retainer.

8. The device according to claim 1, wherein the interchangeable insert is produced as a strand cast profile from aluminium or plastics material.

9. The device according to claim 1, wherein the original profiling is configured as a tongue and groove joint and has at least one projection which is prominent relative to a tongue and groove plane, or said profiling has a recess.

10. The device according to claim 9, wherein the first retainer has at least one retaining projection which upwardly secures the tongue and groove joint and at least partly engages behind the projection or engages into the recess.

11. The device according to claim 10, wherein predetermined breaking points are formed on the at least one retaining rib.

12. The device according claim 1, wherein the interchangeable insert is configured substantially in a U shape and one leg of the U is configured as retaining rib and the other leg of the U is configured as supporting rib.

13. The device according to claim 12, wherein the two legs are joined together by a web and the respective legs have predetermined breaking points.

14. The device according to claim 1, wherein the interchangeable insert has at least one hole to secure the interchangeable insert by an attachment means to a straight edge of a floor covering.

15. The device according to claim 1, wherein the interchangeable insert is held on the base profile by a rail guide system.

16. The device according to claim 15, wherein the rail guide system is a rail arrangement which is spherical in cross section.

17. The device according to claim 15, wherein the rail guide system is a dovetail joint.

\* \* \* \* \*